(12) United States Patent
Li et al.

(10) Patent No.: US 10,806,949 B2
(45) Date of Patent: Oct. 20, 2020

(54) METHOD AND SYSTEM OF GENERATING RADIATION TREATMENT PLAN

(71) Applicant: OUR UNITED CORPORATION, Xi'an (CN)

(72) Inventors: Jinsheng Li, Huntingdon Valley, PA (US); Haifeng Liu, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 423 days.

(21) Appl. No.: 15/351,494

(22) Filed: Nov. 15, 2016

(65) Prior Publication Data

US 2018/0133516 A1    May 17, 2018

(51) Int. Cl.
*A61N 5/00* (2006.01)
*A61N 5/10* (2006.01)

(52) U.S. Cl.
CPC ......... *A61N 5/1081* (2013.01); *A61N 5/1039* (2013.01); *A61N 5/1047* (2013.01); *A61N 5/1082* (2013.01); *A61N 5/1084* (2013.01)

(58) Field of Classification Search
CPC .. A61N 5/1047; A61N 5/1082; A61N 5/1084; A61N 2005/1061; A61N 5/1081
See application file for complete search history.

(56) References Cited

U.S. PATENT DOCUMENTS

| | | | |
|---|---|---|---|
| 5,537,452 A | 7/1996 | Shepherd et al. | |
| 5,818,902 A | 10/1998 | Yu | |
| 6,393,096 B1 | 5/2002 | Carol et al. | |
| 7,280,633 B2 | 10/2007 | Cheng et al. | |
| 7,835,492 B1 | 11/2010 | Sahadevan | |
| 7,876,882 B2 | 1/2011 | Meyer et al. | |
| 7,902,530 B1 | 3/2011 | Sahadevan | |
| 8,139,714 B1 | 3/2012 | Sahadevan | |
| 8,173,983 B1 | 5/2012 | Sahadevan | |
| 2002/0006182 A1 | 1/2002 | Kim et al. | |
| 2003/0219098 A1 | 11/2003 | McNutt et al. | |
| 2016/0038768 A1* | 2/2016 | Liu | A61N 5/1082 378/62 |

FOREIGN PATENT DOCUMENTS

| | | |
|---|---|---|
| CN | 1275410 A | 12/2000 |
| CN | 1355055 A | 6/2002 |

(Continued)

OTHER PUBLICATIONS

Liu, "Multi-Purpose Radiation Therapy System," Jul. 5, 2015. WO2015/062093. (Year: 2015).*

(Continued)

*Primary Examiner* — Dani Fox
(74) *Attorney, Agent, or Firm* — Kolitch Romano LLP

(57) ABSTRACT

The present disclosure discloses a radiation treatment plan generation method, which is applied to a therapeutic equipment comprising at least two therapeutic heads. The method comprises the steps of: acquiring images of an area of the patient with a tumor; determining a treatment target region including the tumor as a region for being irradiated with a radiation beam upon radiotherapy; obtaining a prescription dose of the treatment target, wherein the prescription dose comprises a parameter of prescription dose value that is a magnitude of a dose received by the tumor; and determining a therapeutic head, a therapeutic approach and a therapeutic drive approach suitable for irradiating the target region, based on the therapeutic target region and the prescription dose thereof.

19 Claims, 16 Drawing Sheets

(56) References Cited

FOREIGN PATENT DOCUMENTS

| | | | |
|---|---|---|---|
| CN | 1565670 | A | 1/2005 |
| CN | 1919372 | A | 2/2007 |
| CN | 101861185 | A | 10/2010 |
| CN | 102184334 | A | 9/2011 |
| CN | 102688558 | A | 9/2012 |
| CN | 102698374 | A | 10/2012 |
| CN | 202682584 | U | 1/2013 |
| CN | 102939607 | A | 2/2013 |
| CN | 103119626 | A | 5/2013 |
| CN | 203408368 | U | 1/2014 |
| CN | 104994909 | A | 10/2015 |
| WO | 2015062093 | A1 | 5/2015 |

OTHER PUBLICATIONS

Aug. 13, 2014, International Search Report from the State Intellectual Property Office of China in PCT Application No. PCT/CN2013/086462, which is a related application to this U.S. application.

Nov. 21, 2016, First Office Action from the State Intellectual Property Office of China in Chinese application No. 201380004392.2, which is a related application to this U.S. application.

May 25, 2017, Second Office Action from the State Intellectual Property Office of China in Chinese application No. 201380004392.2, which is a related application to this U.S. application.

Oct. 9, 2019, First Office Action from the State Intellectual Property Office of China in Chinese application No. 201711260030.6, which is a related application to this U.S. application.

Dec. 30, 2019, Second Office Action from the State Intellectual Property Office of China in Chinese application No. 201711260030.6, which is a related application to this U.S. application.

May 9, 2017, Extended European Search Report from the European Patent Office in EP Application No. 13896320.2, which is a foreign counterpart application to this U.S. application.

Mar. 18, 2019, Extended European Search Report from the European Patent Office in EP Application No. 18198900.5, which is a foreign counterpart application to this U.S. application.

Aug. 17, 2017 International Search Report from the State Intellectual Property Office of China in PCT Application No. PCT/CN2016/105935, which is a related application to this U.S. application.

\* cited by examiner

METHOD AND SYSTEM OF GENERATING RADIATION TREATMENT PLAN

CROSS-REFERENCE TO RELATED APPLICATION

This application is a continuation-in-part of U.S. application Ser. No. 14/437,333, filed on Apr. 21, 2015, which is hereby incorporated by reference herein.

TECHNICAL FIELD

The invention relates to the technical field of medical equipment, and more particularly to a method and system of generating radiation treatment plan.

BACKGROUND

Radiation therapy is a common treatment for treating a tumor. There are generally two kinds of radiotherapy for the treatment, one for stereotactic multi-source focused radiation therapy and another for intensity-modulated radiation therapy (IMRT).

Regarding the stereotactic multi-source focused radiation therapy method, a plurality of radiation beams emitting from one multi-source focused treatment head, which is installed on a treatment equipment, are focused to one focal point (namely, the target region), so that high-dose irradiation is performed on the tumor which is in the target region. This multi-source focused radiation therapy method may be adopted to perform high-dose irradiation for tumor tissues while reducing radiation damage for surrounding tissues. This multi-source focused radiation therapy method, with a precise therapeutic property, has a very good therapeutic effect for intracranial tumors or head and neck tumors. However, for a body tumor that has a complicated shape or that is large, the foregoing multi-source focused radiation therapy method has its limits, and the conformal intensity modulated radiation therapy method would be required.

The so-called conformal intensity modulated radiotherapy means that the therapeutic equipment comprises a conformal treatment head, generally an accelerator, and a multi-leaf collimator which is used to form a beam-passable region which is similar to the tumor shape. As such, the area of the target region or at least part of the target region can be irradiated by the radiation beams, to achieve the purpose of conformal treatment.

Currently, there is no radiation therapy device that can integrate the stereotactic multi-source focused radiation therapy method with the conformal and intensity-modulated radiation therapy method. In other words, a single current radiation therapy device cannot implement both accurate multi-source focused therapy and conformal therapy. Therefore, it is impossible to provide different treatment options in the same device for different or same tumors.

SUMMARY

The present invention provides a method of generating a radiation therapy plan and a radiation therapy planning system. The radiation therapy plan is for the purpose of achieving a synergistic therapy with different therapeutic heads on a single radiotherapy equipment which includes a conformal therapeutic head and a focused therapeutic head, to improve the treatment efficiency and treatment effect.

In order to solve the above technical problems, the present invention adopts the following technical scheme:

A radiation treatment plan generation method, applied to a therapeutic equipment comprising at least two therapeutic heads is provided. The method includes the steps of: acquiring images of an area of the patient with a tumor; determining a treatment target region including the tumor as a region for being irradiated with a radiation beam upon radiotherapy; obtaining a prescription dose of the treatment target, wherein the prescription dose comprises a parameter of prescription dose value that is a magnitude of a dose received by the tumor; and determining a therapeutic head, a therapeutic approach and a therapeutic drive approach suitable for irradiating the target region, based on the therapeutic target region and the prescription dose thereof. Wherein, the therapeutic approach comprises at least the type of irradiation technique, time of irradiation and shape of an irradiation field, the therapeutic drive approach comprises synchronous drive approach and asynchronous drive approach, wherein the synchronous drive approach represents emitting radiation beam simultaneously or alternately and completing a treatment by both of the two types of therapeutic heads at the same time period; the asynchronous drive approach represents completing the treatment in different steps each with a therapeutic head, and a treatment process is started after a completion of another treatment process.

A radiation treatment planning system applied to a therapeutic equipment comprising at least two therapeutic heads is further provided. The radiation treatment planning system comprises a processor configured for: acquiring images of an area of the patient with a tumor; determining a treatment target region including the tumor as a region for being irradiated with a radiation beam upon radiotherapy; obtaining a prescription dose of the treatment target, wherein the prescription dose comprises a parameter of prescription dose value that is a magnitude of a dose received by the tumor; and determining a therapeutic head, a therapeutic approach and a therapeutic drive approach suitable for irradiating the target region, based on the therapeutic target region and the prescription dose thereof. Wherein the therapeutic approach comprises at least the type of irradiation technique, time of irradiation and shape of an irradiation field, the therapeutic drive approach comprises synchronous drive approach and asynchronous drive approach, wherein the synchronous drive approach represents emitting radiation beam simultaneously or alternately and completing a treatment by both of the at least two therapeutic heads at the same time period; the asynchronous drive approach represents completing the treatment in different steps each with a therapeutic head, and a treatment process is started after a completion of another treatment process.

The method and system of generating radiation treatment plan is provided. The method of generating radiation treatment plan includes: acquiring body images of the patient; determining at least part of the vital organs surrounding the treatment target region based on the acquired images; obtaining a prescription dose of the treatment target and the corresponding dose limits for the vital organs; determining a therapeutic head, a therapeutic approach and a therapeutic drive approach suitable for irradiating the target region, based on the therapeutic target region and the prescription dose thereof. Wherein, the therapeutic approach comprises at least the type of irradiation technique, time of irradiation and shape of an irradiation field. The therapeutic drive approach comprises synchronous drive approach and asynchronous drive approach. With the method of generating radiation treatment plan, it is possible to perform a synergistic treatment of the tumor by the two types of therapeutic heads, and further optimize the radiation treatment plan. Therefore, it is possible to reduce the position error caused by multiple positioning processes during multiple treatments with a focused therapeutic head and a conformal therapeutic head, improving the accuracy and efficiency of treatment, and further achieve more efficient and accurate treatment.

BRIEF DESCRIPTION OF THE DRAWINGS

In order to more clearly illustrate the embodiments of this invention or the technical schemes of the existing technology, figures used in the embodiments of the invention or the existing technology will be briefly described below. Obviously, the figures described below are some embodiments of this invention. For those skilled in the art, other figures may still be obtained based on these figures without providing any creative and labor effort.

DETAILED DESCRIPTION

For making the purpose, the technical proposal and advantages of embodiments of the invention more clear, the technical proposal of the embodiments of this invention may be described clearly and fully using the figures included. Clearly, the described embodiments are only parts of the embodiments of this invention and not all of the embodiments. Based on the embodiments of this invention, all other embodiments obtained without contributing any creative effect by those skilled in the art are within the scope of protection of this invention.

The present disclosure provides a radiation treatment plan generation method according to the embodiments thereof, for use in a radiotherapy equipment comprising at least two therapeutic heads.

Figure 1:
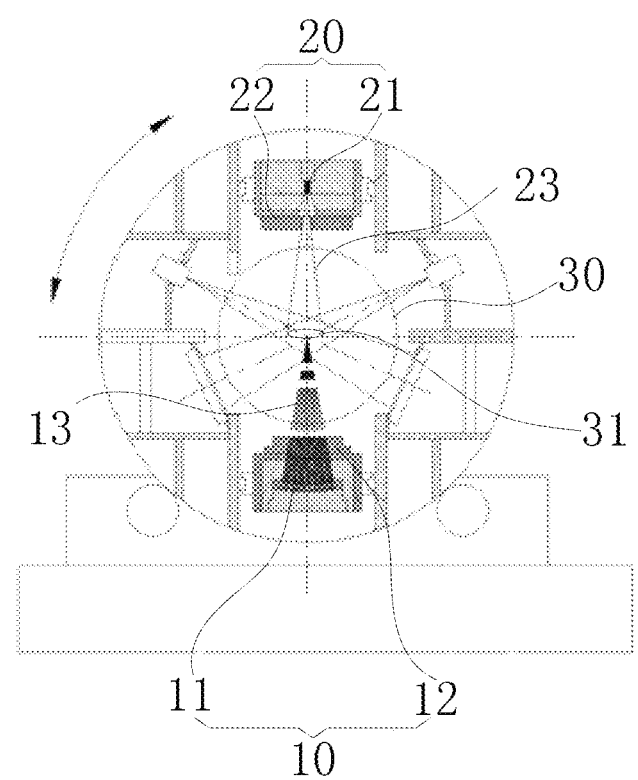
FIG. 1 is a schematic view of a radiation equipment, according to one embodiment of the present disclosure.
Figure 2:
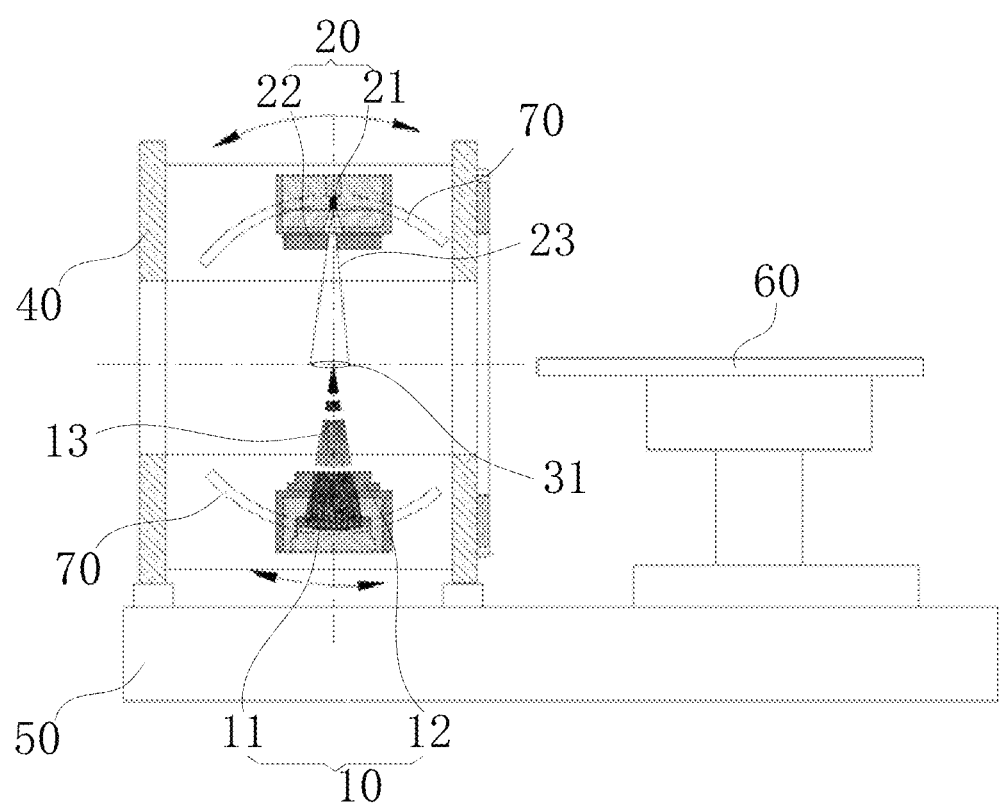
FIG. 2 is a schematic view of the radiation equipment, according to another embodiment of the present disclosure.

In this embodiment, the radiotherapy equipment comprises at least two types of therapeutic heads with at least one focused therapeutic head and at least one conformal therapeutic head. For example, the radiotherapy equipment may include a focused therapeutic head and a conformal therapeutic head, or the radiotherapy equipment may include two focused therapeutic heads and a conformal therapeutic head, or alternatively, the radiotherapy equipment may include two focused therapeutic heads and two conformal therapeutic heads. As illustrated in FIGS. 1 and 2, the present disclosure is illustrated by the example of the radiotherapy equipment 100 including a focused therapeutic head 10 and a conformal therapeutic head 20 positioned oppositely.

Generally, a focused therapeutic head generally refers to that the therapeutic head comprises a plurality of radiation sources, each of which emits a radiation beam which respectively focuses on a focal point corresponding to a different region of the tumor so as to achieve a radiation therapy to different regions of the tumor. In generally, the focal point is corresponding to a target region, for achieving a high-dose irradiation of the target region. A conformal therapeutic head generally refers to a therapeutic head comprising a radiation source emitting a scattered cone beam, and a collimator or a multi-leaf collimator configured therein forming a beam-passable region similar to the shape of the tumor. The cone beam is irradiated to the tumor through the beam-passable region, thereby realizing the radiation therapy of the tumor.

Referring to FIGS. 1 and 2, the focused therapeutic head 10 includes a plurality of first radiation sources 11 each being capable of emitting a first radiation beam 13. The field diameter of the first radiation beam 13 can be adjusted through a collimator 12. The plurality of first radiation beams 13 are focused on a focal point that is irradiated on a partial region of the tumor 31 of the human body 30. The conformal therapeutic head 20 includes a second radiation source 21 that emits a scattered cone beam 23. A collimator or a multi-leaf collimator forms a beam-passable region which is similar to the tumor shape. As such, the tumor can be irradiated by passing the cone beam 23 through the beam-passable region, to achieve the purpose of conformal treatment.

Figure 3:
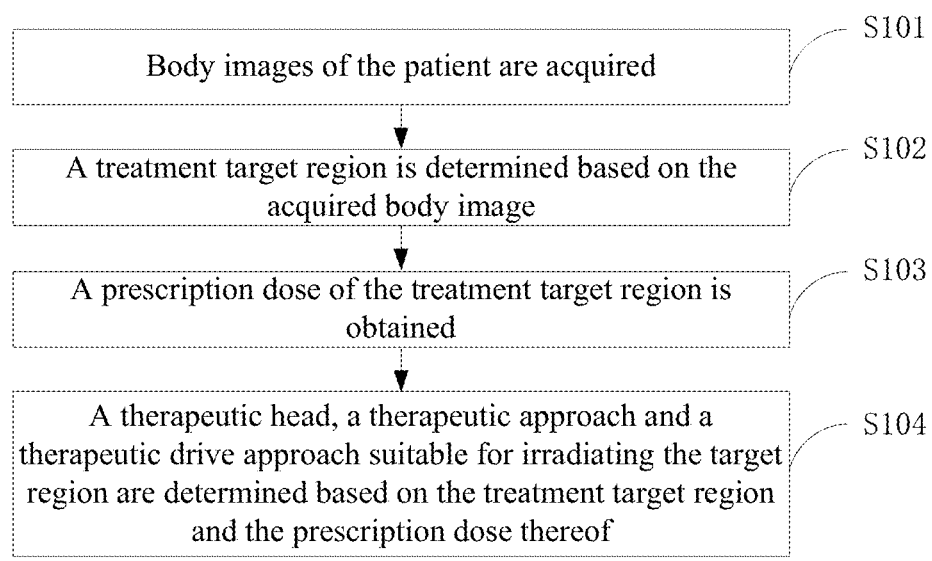
FIG. 3 is a schematic diagram of a radiation treatment plan generation method, according to an embodiment of the present disclosure.

As shown in FIG. 3, the present disclosure provides an embodiment of the method of generating radiation therapy plan. The method includes the steps of S101 to S104.

In step S101, body images of the patient are acquired. The body images include images of the tumor. Typically, the body image refers to a body image that includes the tumor area. As an example, in the present disclosure, the body image is an image of any part or the whole body of the patient. Illustratively, the body image could be a head image of the patient and/or a body image of the patient.

The body images are generally three-dimensional images, e.g. CT, MR or PET images, etc. The body images could be imported into a treatment planning system of the treatment equipment. In the present embodiment, the CT image is performed with a density conversion according to the material density calibration curve of the CT equipment. The other images are fused and registered with the primary images, such as the CT images which are used for the plan, to ensure the images of the same patient can be accurately registered overlapping, especially in the region of interest (e.g. treatment area of the tumor and vital sensitive organs or tissues), to ensure that all of the locations of the anatomy structure of the patient in the region of interest are uniform across all images.

Specifically, the fusion and registration for different images are aimed at accurately locating the patient's anatomy structure, and determining the boundary of the tumor, the morphology of the tumor, distribution characteristics and the location and shape of the healthy tissue with the help of the characteristics of different image forms, providing a foundation for accurately determining the target region, precise treatment plan and avoidance of sensitive organs.

In step S102, a treatment target region is determined based on the acquired body image. The treatment target region comprises the tumor and is a region being irradiated with the radiation beams during radiotherapy.

Illustratively, based on the acquired images, oncologist uses the radiotherapy system to divide the tumor and the surrounding tissue according to the complexity of the tumor and surrounding tissue, delineating the treatment target region. As such, the system can directly obtain the treatment target region according to the acquired body image. It is understood that the tumor and the surrounding tissues can be identified with different colors, and the treatment target region can be automatically draw out based on a system algorithm, for example, coloring the tumor and the surrounding tissues, which is stored in a computer.

Illustratively, the step of determining the treatment target region may include: determining the complexity of the tumor and surrounding tissues, and dividing the tumor and the surrounding tissues, or, determining a characteristic region within the tumor based on functional images and other diagnostic information, in order to carry out targeted treatment of these areas, such as increasing the dose or changing the grading, etc. Wherein, the characteristic region includes an anoxic region, a tumor cell intensive region, etc. Regarding the presence of distal metastases and multiple disconnected target regions, different treatment plans and fractional therapeutic doses may also be used depending on the characteristics of each target region.

In step S103, a prescription dose of the treatment target region is obtained. Wherein the prescription dose comprises a parameter of prescription dose value, that is the magnitude of the dose that the tumor should be received in order to achieve a therapeutic effect.

Illustratively, the prescription dose will vary according to the type and location of the cancer cells. The value of the dose is generally determined based on the particular characteristics of the tumor. In general, the value of the prescription dose may be input by an attending physician. Of course, the value of the prescription dose may also be selected based on the parameter values of the tumor by referring a previously stored template.

In step S104, a therapeutic head, a therapeutic approach and a therapeutic drive approach suitable for irradiating the target region are determined based on the treatment target region and the prescription dose thereof.

Wherein, the therapeutic approach comprises the type of irradiation technique, time of irradiation and shape of an irradiation field. Illustratively, the therapeutic drive approach comprises a synchronous drive approach and an asynchronous drive approach. Wherein, the synchronous drive approach represents emitting radiation beam simultaneously or alternately and completing a treatment by both of the two therapeutic heads at the same time period. For example, using the conformal therapeutic head to perform a conformal treatment to a large area of the tumor, and using the focused therapeutic head to perform a dose enhancement treatment on part of the tumor, increasing the local dose of the tumor, e.g. applying the local dose enhancement treatment to the anoxic region, the tumor cell intensive region, or the like. The asynchronous drive approach represents completing the treatment in different steps each with a therapeutic head, and a treatment process is started after a completion of another treatment process. For example, if the tumor is large, the conformal therapeutic head is applied at first for large-scale conformal treatment. In the irradiation process, if part of the tumor region receives less dose due to uneven dose distribution, or it is needed to perform dose-enhanced to the anoxic region and/or tumor cell intensive areas, the local dose-enhanced radiation therapy can be started with the focused therapeutic head after completing the conformal treatment.

The irradiation technology refers to different irradiation methods, including whole-arc irradiation, partial-arc irradiation and directional irradiation with the focused therapeutic head, etc., and also including a three-dimensional conformal treatment, stereotactic intensity modulated therapy and intensity modulated arc therapy of the conformal therapeutic head, and so on.

Figure 5:
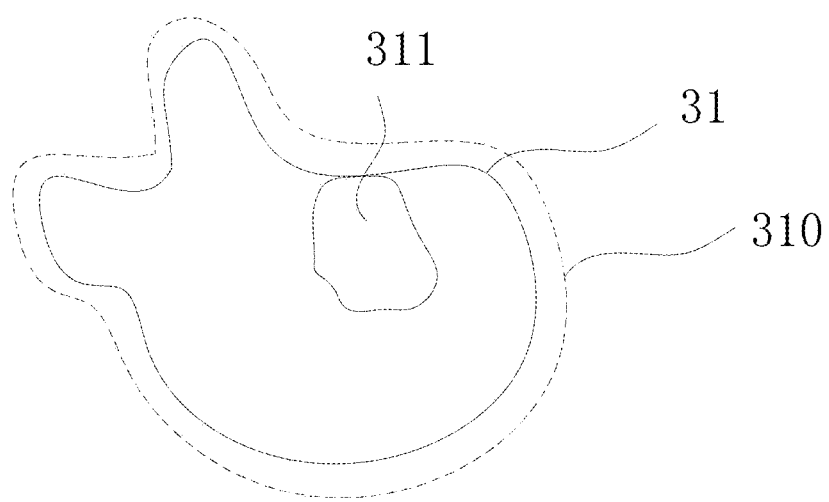
FIG. 5 is a schematic view of a treatment target region of the present disclosure.

For the focused therapeutic head, the radiation field is generally circular in shape with several selectable sizes. For the conformal therapeutic head, the radiation field is generally formed in an arbitrary shape formed by the multi-leaf collimator. As shown in FIG. 5, in general, the target region 310 illuminated to the body after being conformed is larger than the tumor 31. The longer the irradiation time, the more radiation the human body receives. Therefore, the shape of the radiation field and the length of the irradiation time would directly affect the amount of radiation received by the human body.

Illustratively, in step S104, the type of the therapeutic head, the therapeutic approach, and the therapeutic drive approach may be determined by the parameters inputted by the attending physician. In other embodiments, it can also be a treatment plan with determined therapeutic head, therapeutic approach and therapeutic drive approach automated by the system based on the prescription dose of the target region and through an automated optimization and iterations of a reverse planning process.

The radiotherapy equipment of the present disclosure comprises the focused therapeutic head and the conformal therapeutic head, and the focused therapeutic head has a more precise advantage for treating small tumors, and the conformal therapeutic head can better perform tumor conformal treatment for large tumors. Therefore, in the present disclosure, during establishing the treatment plan for a tumor, it is possible to achieve more efficient and more accurate treatment by using a focused therapeutic head, a conformal therapeutic head or a combination thereof according to a specific image of the tumor. By this, it is possible to reduce the errors caused by multiple positioning errors and improve the accuracy and speed of radiation therapy.

The present disclosure provides the radiation treatment plan generation method, applied to the radiotherapy equipment comprising at least two therapeutic heads. In this embodiment, the two therapeutic heads is respectively the focused therapeutic head and the conformal therapeutic head. The radiation treatment plan generation method comprises the steps of: acquiring images of an area of the patient with a tumor; determining a treatment target region including the tumor as a region for being irradiated; obtaining a prescription dose of the treatment target; determining a therapeutic head, a therapeutic approach and a therapeutic drive approach suitable for irradiating the target region based on the treatment target region and the prescription dose thereof. Wherein, the therapeutic approach comprises the type of irradiation technique, time of irradiation and shape of an irradiation field. The therapeutic drive approach comprises the synchronous drive approach and the asynchronous drive approach. By using the radiation treatment plan generation method disclosed in the present disclosure, it is possible to achieve more efficient and more accurate treatment by using a focused therapeutic head, a conformal therapeutic head or a combination thereof according to a specific image of the tumor. With this, it is possible to reduce the errors caused by multiple positioning errors and improve the accuracy and speed of radiation therapy.

A dose or a dose distribution for the treatment plan is calculated based on the determined therapeutic head, therapeutic approach, and therapeutic drive approach, to determine whether the dose or a dose distribution for the treatment target region meets a requirement of the prescription dose. If the dose or dose distribution of the treatment target region does not meet the requirement of the prescription dose, the therapeutic head, therapeutic approach, and therapeutic drive approach are adjusted such that the dose or dose distribution of the treatment target region meets the requirements of the prescription dose. The dose distribution will be described in the following paragraphs in detail.

Figure 4:
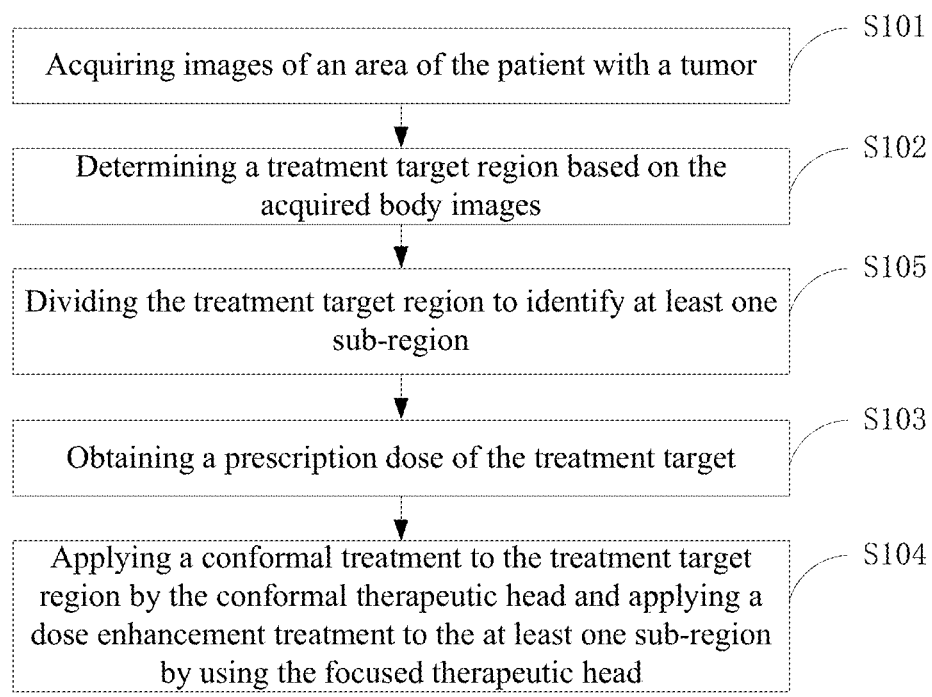
FIG. 4 is a schematic diagram of the radiation treatment plan generation method according to another embodiment of the present disclosure.

As shown in FIG. 4, after the step of S102 and before the step S104, the method of generating the treatment plan further includes step S105.

In step S105, the treatment target region is subdivided to identify at least one sub-region.

It should be noted that in step S103 above, the prescription dose also includes a prescribed dose distribution, that is, the dose that should be received for different sub-regions of the treatment target region to achieve a therapeutic effect. And, said step S104 may specifically executed by a conformal therapeutic head to perform a conformal treatment to the target region and using a focused therapeutic head to perform a localized dose-enhancement treatment for the sub-regions within the treatment target region.

It should be noted that, the step S105 is perform after step S102 and before step S104. That is to say, the step S105 may be performed before step S103 or after step S103 or simultaneously performed with step S103. The embodiments of the present disclosure will not specifically limit the sequence of the steps in the drawings, but will be described in detail with reference to the accompanying drawings.

Take FIG. 5 as an example, the treatment target region 310 is subdivided, e.g., the treatment target region 310 is divided with a sub-region 311 as an anoxia region and other regions excluding the sub-region 311. In order to achieve the effect of eliminating the tumor, the local dose of the sub-region 311 should be more than the dose for other regions. In the radiation treatment plan generation method of the present disclosure, a conformal treatment of the tumor could be performed by the conformal therapeutic head, and at the same time, the local dose enhancement treatment for each sub-region could be performed by the focused therapeutic head. For example, the multi-leaf collimator may be conformed to form a beam-passable region similar to the tumor 31, and the radiation source of the conformal therapeutic head emits a radiation beam that is illuminated on the body through the beam-passable region, to form a treatment target region 310 shown in FIG. 5. As such, the treatment target region 310 can be treated with a conformal therapy. The focal point of focused therapeutic head is then directed toward the sub-region, thereby enhancing the dose of the sub-region.

The method for generating a treatment plan provided by the present disclosure can realize division of the treatment target region and realize the conformal treatment of the treatment target region by using the conformal therapeutic head and realize the dose enhancement treatment of the sub-region of the treatment target region by the focusing therapeutic head. As such, the best possible synergistic treatment of the tumor can be achieved within a single-time treatment. Therefore, it is possible to avoid the position error caused by multiple treatments and positioning during the treatment, improving the accuracy and efficiency of treatment.

Figure 6:
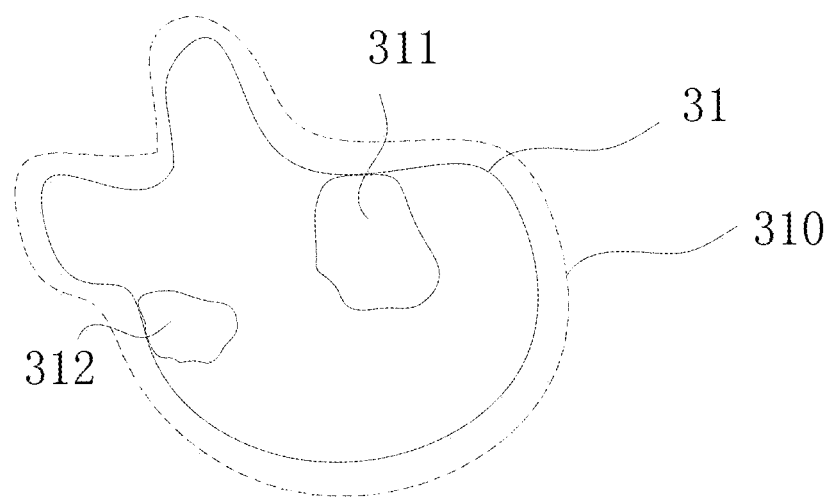
FIG. 6 is a schematic view of another treatment target region of the present disclosure.

It is to be noted that, in the step of dividing the treatment target region to identify at least one sub-region, it can be only one sub-region 311 to be determined as shown in FIG. 5, however, it also can be that two sub-regions are determined, i.e. sub-region 311 and sub-region 312, as shown in FIG. 6. Of course, depending on the particular shape of the tumor, it is also possible to determine a plurality of sub-regions. In the following example, the treatment target region includes two sub-regions.

Refer to FIG. 6, for the radiation treatment plan generation method of the present disclosure, in the case where the treatment target region 310 comprises two or more sub-regions 311 and 312, the step of applying dose enhancement therapy to the sub-region by using the focused therapeutic head comprises: performing the dose enhancement therapy for at least two of the sub-regions. Wherein the therapeutic approach of the focused therapeutic head further comprises moving the focal point to different sub-regions.

Illustratively, if the synchronous drive approach is employed with the focused therapeutic head and the conformal therapeutic head to perform a radiation therapy to the tumor as shown in FIG. 6, the conformal therapeutic head may be employed to conformally irradiate the target region, and during the conformal irradiation process, the focused therapeutic head may be moved between the sub-region 311 and the sub-region 312, such that both the sub-region 311 and the sub-region 312 undergo local dose enhancement.

Furthermore, in the present disclosure, the treatment equipment includes the focused therapeutic head and conformal therapeutic head, wherein the number of the focused therapeutic head and/or the therapeutic head may be two or more. As shown in FIG. 6, in the case where the treatment target region 310 includes at least two sub-regions 311, 312, the conformal treatment of the treatment target region may also be performed using one of the conformal therapeutic heads, and the local dose-enhanced therapy to the sub-region of the treatment target region would be performed by another conformal therapeutic head.

Figure 7:
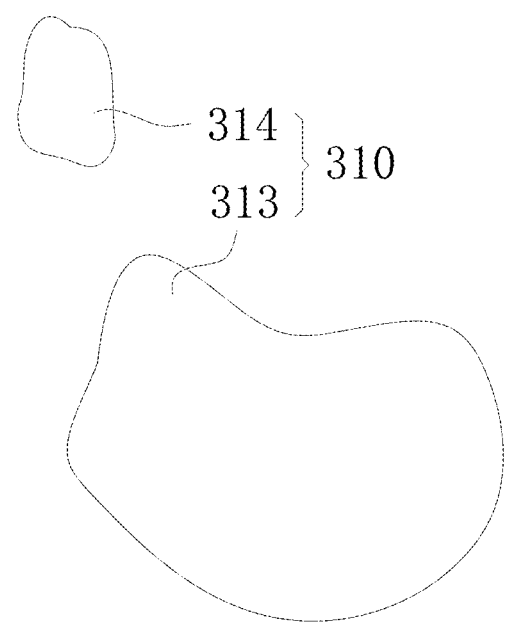
FIG. 7 is a schematic view of another treatment target region of the present disclosure.

Typically, the tumor is easily metastasized to form a plurality of disconnected target regions, such as two or more. As shown in FIG. 7, take the target region 310 including two disconnected sub-regions 313 and sub-regions 314 as an example. The present disclosure provides a radiation treatment plan generation method in which the target region comprises a plurality of disconnected sub-regions. In this case, the step of determining the therapeutic head suitable for the target region comprises: applying different therapeutic heads to different sub-regions.

As shown in FIG. 7, the sub-region 313 may be subjected to conformal treatment using a conformal therapeutic head, and the sub-region 314 may be applied the focused irradiation treatment using the focused therapeutic head. In general, in a case where the widest diameter of the target region is equal to or more than 5 cm, the treatment is performed using the conformal therapeutic head; and when the widest diameter of target region is less than 5 cm, the treatment is performed using the focused therapeutic head.

In the present disclosure, it is disclosed that different sub-regions may be treated with different therapeutic heads. However, it could also be that different sub-regions may be treated with same type of therapeutic heads. Please see FIG. 7, the radiotherapy equipment includes two conformal therapeutic heads. In the treatment process, one of the conformal therapeutic heads could be employed to perform conformal treatment to the sub-region 313, while another conformal therapeutic head is employed to perform conformal treatment to the sub-region 314. Alternatively, in that case that the radiotherapy equipment comprises two focused therapeutic heads, one of the focused therapeutic heads may be used to perform focused radiation therapy to the sub-region 313, and the other focusing therapeutic head may be used to perform focused radiation therapy to the sub-region 314.

Figure 8:
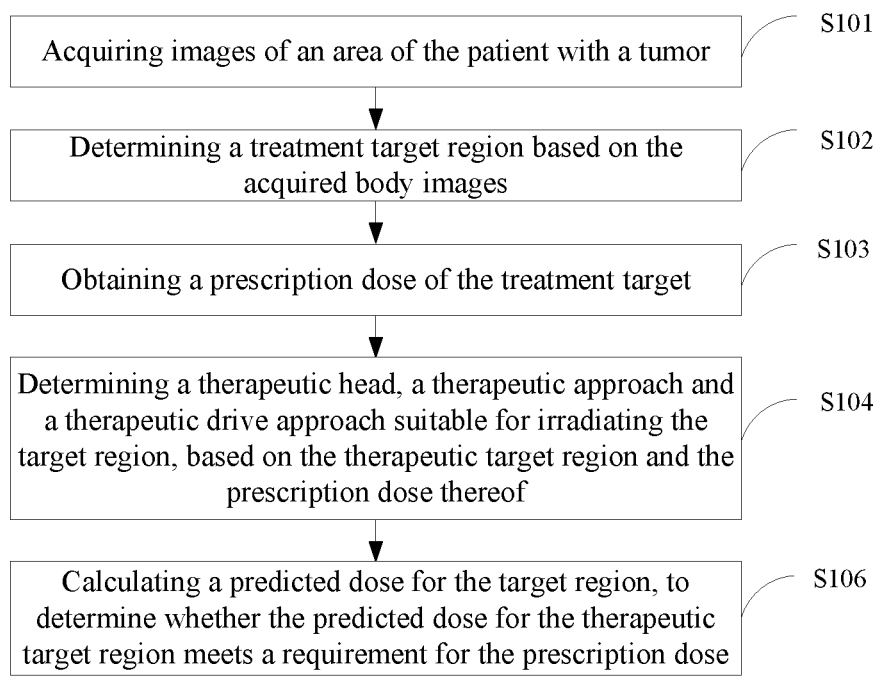
FIG. 8 is a schematic diagram of the radiation treatment plan generation method, according to another embodiment of the present disclosure.

As shown in FIG. 8, the method for generating a treatment plan according to the present disclosure further includes step S106.

In step S106, a predicted dose of the treatment target region is calculated based on the determined therapeutic head, therapeutic approach, and therapeutic drive approach, to determine whether the predicted dose in the treatment target region meets a requirement of the prescription dose.

In the case that the predicted dose does not meet the requirement for the prescription dose, at least one of the therapeutic head, the therapeutic approach, and the therapeutic drive approach would be adjusted such that the dose or dose distribution of the treatment target region meets the requirements of the prescription dose.

Wherein, the predicted dose received by the tumor is generally measured according to the radiation dose of the beams emitted from the radiation source and the dose of the beam through the body, to further determine whether the dose meets the prescription dose requirements. In general, the predicted dose corresponds to the prescription dose. For example, if the prescription dose includes a parameter of prescription dose value and a parameter of prescription dose distribution, the predicted dose may include a parameter of predicted dose value and a parameter of predicted dose distribution. In the present disclosure, the dose distribution of a patient after treatment is predicted based on the dose calculation approach, to determine whether dose distribution meets the prescription dose requirements, to further determine whether the treatment of patients can achieve the desired therapeutic effect.

Figure 9:
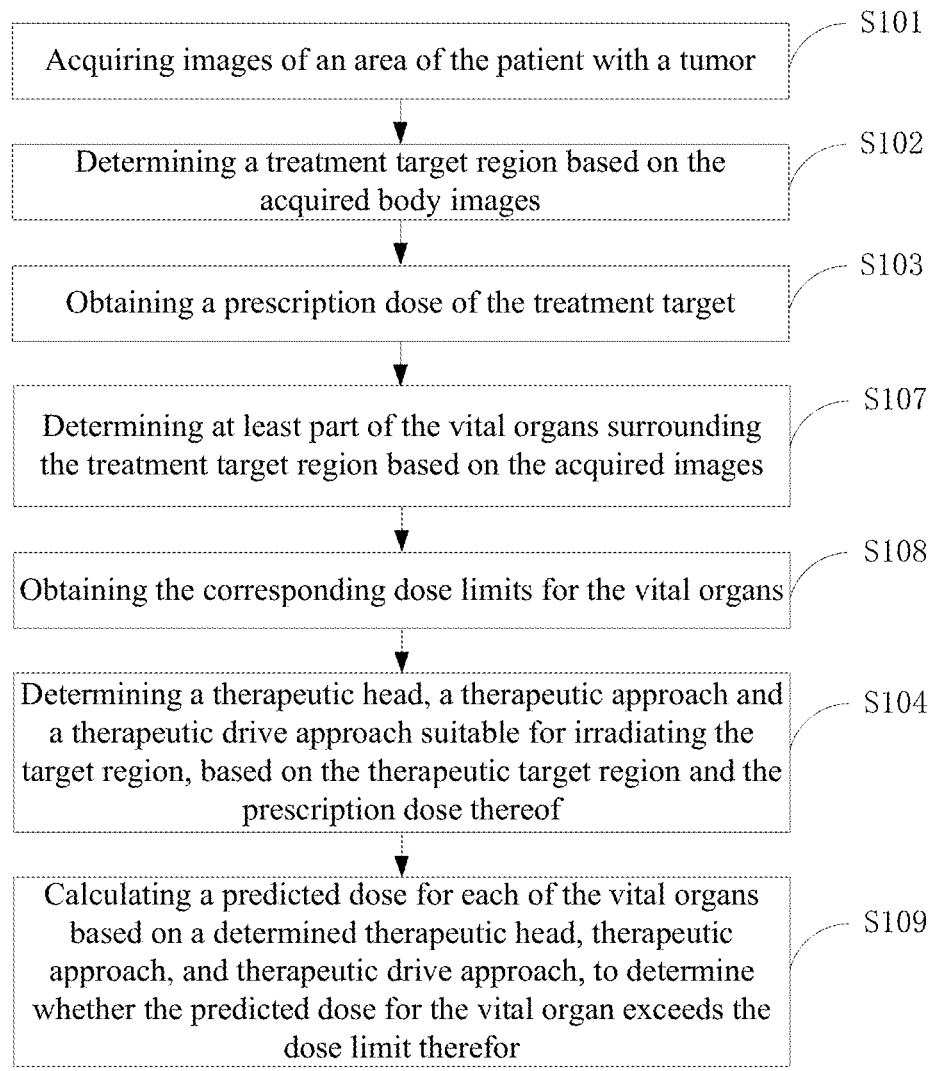
FIG. 9 is a schematic diagram of the radiation treatment plan generation method, according to another embodiment of the present disclosure.

As shown in FIG. 9, the method for generating a treatment plan according to the present disclosure further includes the following steps of S107 to S109.

In step S107, the vital organs surrounding the treatment target region are determined based on the acquired images.

In step S108, a dose limit for the vital organ is obtained. The dose limits for vital organs are intended to avoid serious damage to vital organs by radiation, thus protecting vital organs.

In step S109, a predicted dose value for a vital organ is calculated based on a determined therapeutic head, therapeutic approach, and therapeutic drive approach, and it is further determined that whether the predicted dose value for the vital organ exceeds the dose limit for the vital organ.

If the predicted dose exceeds the dose limit of the vital organ, at least one of a therapeutic head, a therapeutic approach, and a therapeutic drive approach would be adjusted, such that the dose or dose distribution of the vital organ does not exceed the dose limit and avoiding over damage to the vital organ and impact the effect of the image treatment.

It is noted that in the case where the method of generating the treatment plan includes the steps of S107, S108 and S109, but the order of the steps is not limited herein, and FIG. 9 is just shown as an example. For example, step S103 and step S107 may be performed at the same time, or step S107 may be performed before step S103 in the method of FIG. 9.

Figure 10:
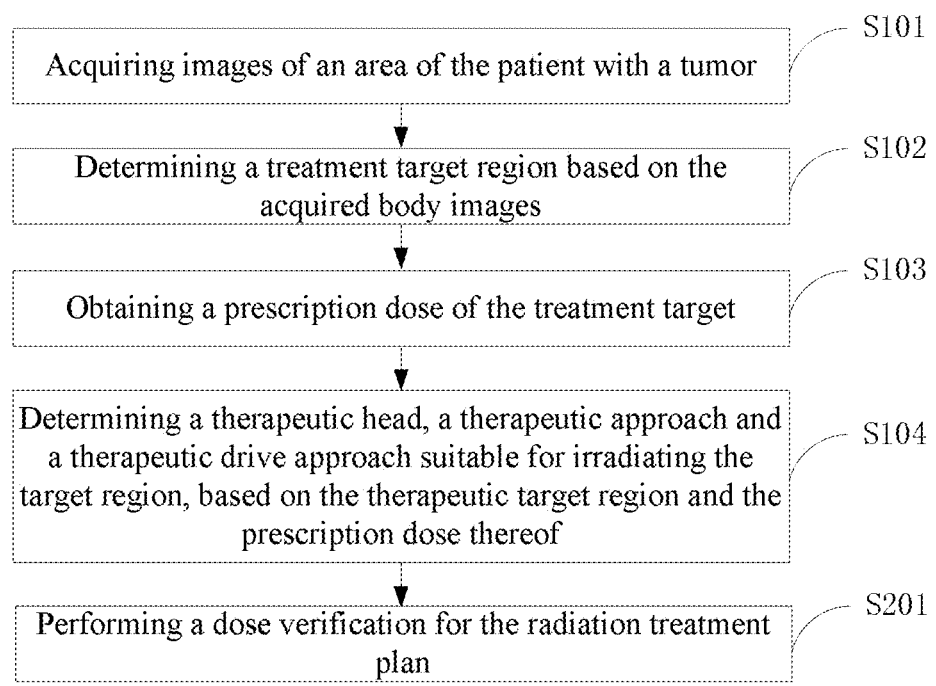
FIG. 10 is a diagram of the radiation treatment plan generation method, according to another embodiment of the present disclosure.

As shown in FIG. 10, the radiation treatment plan generation method in the present disclosure further comprises step S201.

In step S201, the treatment plan is subjected to dose verification.

Dose verification of the treatment plan is generally referring to validate the prescription dose, mainly by verifying the value of the dose and distribution of the dose, to match the radiotherapy equipment with the treatment plan and further determine the accuracy of the treatment plan. In addition, the dose verification can also confirm the accuracy of the dose distribution predicted by the treatment planning system, the correctness of the treatment parameters transmitted between the different systems, and the correctness of the equipment to implement the treatment plan. As such, if the results of dose verification are not satisfactory, it is possible to check and confirm each step.

Take the conformal treatment as an example, if the movement position accuracy of the leaf of the multi-leaf collimator is deviated from a standard, the measured dose distribution would be different. The method of generating the treatment plan provided by the present disclosure is carried out by dose verification of the treatment plan, so as to adjust the treatment plan according to the situation of the equipment, to meet the treatment requirement.

Figure 11:
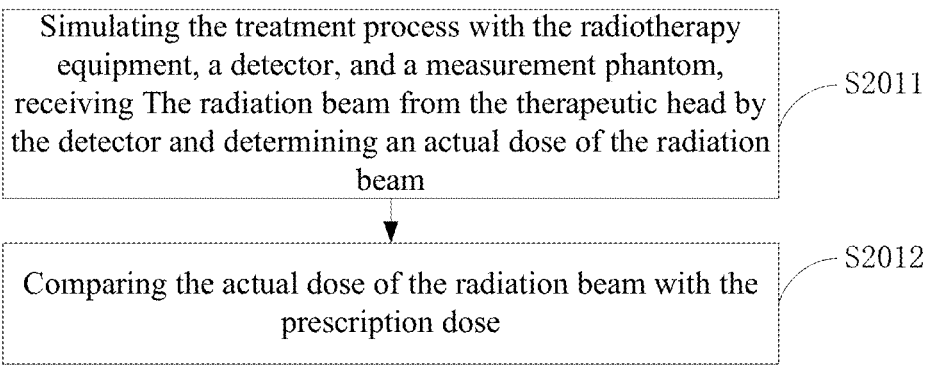
FIG. 11 is a schematic diagram of a method of dose verification provided by the present disclosure.

Illustratively, as shown in FIG. 11, the dose verification of the treatment plan specifically includes steps S2011 and S2012.

In step S2011, the treatment process is simulated with the radiotherapy equipment, a detector, and a measurement phantom. Wherein the detector receives the radiation beam from the therapeutic head and determines an actual dose of the radiation beam. Wherein, the actual dose includes a parameter of dose value and/or dose distribution. In some embodiments, the dose verification of the treatment plan may also involve receiving the radiation beam from the therapeutic head and determining the actual dose of the radiation beam by the radiotherapy equipment. In the present disclosure, it is also possible to simulate the irradiation of the human body using the phantom, to exercise the real therapeutic process. As such, the verification result would be closer to the actual result.

Herein, the detector may be fixedly mounted on the radiotherapy equipment or may be a movable detector that is temporarily used only when the radiotherapy equipment is performing the verification. Take the conformal therapeutic head as an example, the radiotherapy equipment comprises a conformal therapeutic head and a detector positioned opposite the conformal therapeutic head, such that the radiation beams emitted from the conformal therapeutic head is received by the detector through the measurement phantom. The detector determines the actual dose including the value of dose and the dose distribution, based on the received beams.

In step S2012, the actual dose is compared with the prescription dose.

If the verification result does not meet the requirement of the prescription dose, at least one of the therapeutic head, the therapeutic approach, and the therapeutic drive approach is adjusted.

Illustratively, according to the value of the dose and the dose distribution which are determined by the detector, a comparison is made between the prescribed dose and the actual dose, to determine whether the actual dose meets the prescription dose requirement. If the actual dose does not meet the prescription dose requirement, the treatment plan can be adjusted and optimized.

Of course, the dose verification can also be performed in other ways, for example, by directly using the therapeutic head to emit the radiation beams and receiving the radiation beams by the detector for dose verification, thereby the dose verification can be performed by a pre-stored algorithm or the like. The present disclosure is described above illustratively.

Figure 12:
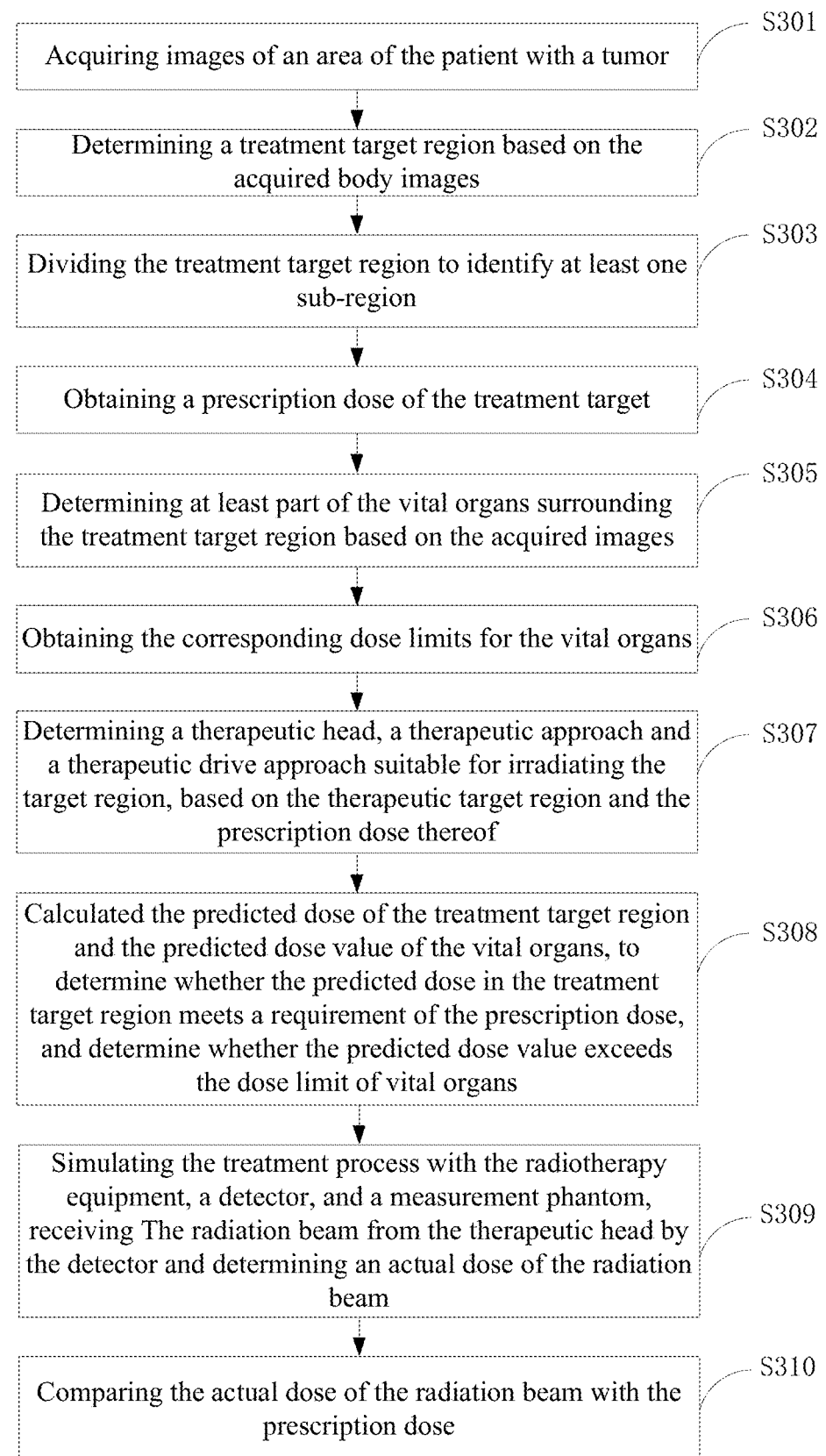
FIG. 12 is a schematic diagram of the radiation treatment plan generation method, according to a specific embodiment of the present disclosure.
Figure 13:
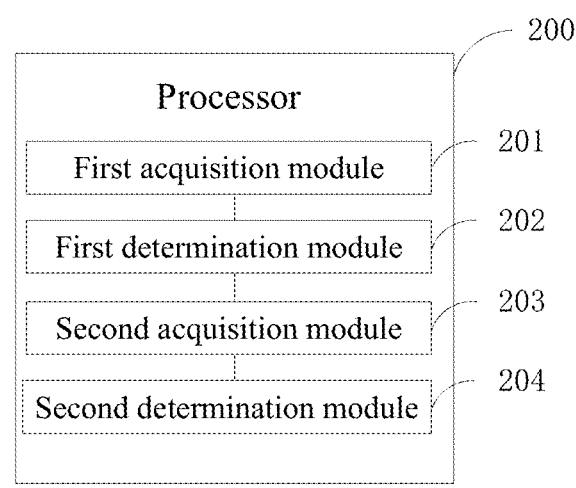
FIG. 13 is a schematic diagram of a processor in accordance with one embodiment of the present disclosure.

As below, a detailed embodiment is mentioned to describe the radiation treatment plan generation method. In this embodiment, the treatment target region 310 includes at least two sub-regions 311 and 312 which can be referred to FIG. 6. As shown in FIG. 12, the method comprises steps of S301 to S310.

In step S301, body images of the patient are acquired. More specifically, step S101 described above can be taken as a reference.

In step S302, in step S102, a treatment target region is determined based on the acquired body image. More specifically, step S102 described above can be taken as a reference.

In step 303, the treatment target region is subdivided to identify at least one sub-region. More specifically, step S105 described above can be taken as a reference.

In step S304, the prescription dose of the treatment target region is obtained. Wherein, the prescription dose comprises a parameter of prescription dose value and a parameter of prescription dose distribution. The prescription dose value is the magnitude of that the tumor should be received in order to achieve the expected therapeutic effect. The prescription dose distribution is the dose that should be received for the different sub-regions of the treatment target region to achieve the expected therapeutic effect.

Referring to FIG. 6, the treatment target region 310 comprises two or more sub-regions 311 and 312. The sub-region 311 is an anoxic region, and the sub-region 312 is a tumor cell intensive region. As such, the distribution of the prescription dose for these corresponding sub-regions 311, 312 would be greater than that of the other regions.

In step S305, the vital organs surrounding the treatment target region are determined based on the acquired images. More specifically, step S107 described above can be taken as a reference.

In step S306, the dose limit for the vital organ is obtained. Specifically, step S108 described above can be taken as a reference.

In step 307, the therapeutic head, the therapeutic mode, and the therapeutic drive mode suitable for the target region are determined based on the treatment target region and the prescription dose thereof.

In particular, because of the need for local dose enhancement of the sub-regions 311, 312 of the treatment target region, a combination of the focused therapeutic head and the conformal therapeutic head may be selected for treatment of the target region. Conformal treatment to the treatment target region is performed by the conformal therapeutic head, and the local dose enhancement treatment to the sub-regions 311, 312 is performed by the focused therapeutic head. The drive mode may be synchronous drive mode, i.e., driving the focused therapeutic head and the conformal therapeutic head simultaneously, and moving the focal point of the focus therapeutic head between the sub-regions 311 and 312 during treatment.

In step S308, the predicted dose of the treatment target region and the predicted dose value of the vital organs are calculated based on determined therapeutic head, therapeutic approach, and therapeutic drive approach, to determine whether the predicted dose in the treatment target region meets a requirement of the prescription dose, and determine whether the predicted dose value exceeds the dose limit of vital organs.

That is, the dose value and the dose distribution in the treatment target region are determined to meet the requirements of the prescription dose, to achieve the necessary therapeutic effect. In addition, whether the predicted dose of vital organs exceeds the dose limit of vital organs is predicted, for preventing an excessive dose from leading serious damage to the vital organs and bringing other harm to the patients.

In the case that the predicted dose does not meet the requirement for the prescription dose, at least one of the therapeutic head, the therapeutic approach, and the therapeutic drive approach would be adjusted such that the dose or dose distribution of the treatment target region meets the requirements of the prescription dose.

If the predicted dose exceeds the dose limit of the vital organ, at least one of a therapeutic head, a therapeutic approach, and a therapeutic drive approach would be adjusted, such that the dose or dose distribution of the vital organ does not exceed the dose limit and avoiding over damage to the vital organ and impact the effect of the image treatment.

That is, treatment plan was able to implement only when the prescription dose requirements and the restriction requirements of vital organs are met at the same time, if one of them is not met, it is needed to adjust the treatment plan.

In step S309, the treatment process is simulated with the radiotherapy equipment, a detector, and a measurement phantom. Wherein the detector receives the radiation beam from the therapeutic head and determines an actual dose of the radiation beam. Wherein, the actual dose includes a parameter of dose value and/or dose distribution. Specifically, step S2011 described above can be taken as a reference.

In step S310, the actual dose is compared with the prescription dose. Specifically, step S2012 described above can be taken as a reference.

The comparison is made between the prescribed dose and the actual dose according to the value of the dose and the dose distribution which are determined by the detector, to determine whether the actual dose meets the prescription dose requirement. If the actual dose does not meet the prescription dose requirement, the treatment plan can be adjusted and optimized.

The treatment plan corresponding to the treatment target region as shown in FIG. 6 is generated under satisfying the conditions in above steps, and the treatment plan is controlled by the treatment planning system to treat the patient.

In the following, the present disclosure provides the treatment planning system corresponding to the radiation treatment plan generation method described above. It should be noted that each of the functional units included in the following treatment planning system may perform the corresponding steps in the method described above. Therefore, the various functional units of the system will not be described in detail.

The present disclosure provides a radiation treatment planning system, applied to the radiotherapy equipment which comprises at least two therapeutic heads. The system comprises a processor comprising the following modules.

A first acquisition module 201 is configured for acquiring images of an area of the patient with a tumor.

The body image is generally three-dimensional images, e.g. CT, MR or PET images, etc. The body images could be imported into a treatment planning system of the treatment equipment. In the present embodiment, the CT image is performed with a density conversion according to the material density calibration curve of the CT equipment. The other images are fused and registered with the primary images, such as the CT images which are used for the plan, to ensure that images of the same patient can be accurately registered overlapping, especially in the region of interest (e.g. treatment area of the tumor and vital sensitive organs or tissues), to ensure that all of the locations of the anatomy structure of the patient in the region of interest are uniform across all images.

A first determination module 202 is configured for determining a treatment target region including the tumor as a region for being irradiated with a radiation beam upon radiotherapy.

Generally, based on the acquired images, the oncologist uses the radiotherapy system to divide the tumor and the surrounding tissue according to the complexity of the tumor and surrounding tissue, delineating the treatment target region. As such, the system can directly obtain the treatment target region according to the acquired body image. It is understood that the tumor and the surrounding tissues can be identified with different colors, and the treatment target region can be automatically draw out based on a system algorithm, for example, coloring the tumor and the surrounding tissues, which is stored in a computer.

A second acquisition module 203 is configured for obtaining a prescription dose of the treatment target, wherein the prescription dose comprises a parameter of prescription dose value that is a magnitude of a dose received by the tumor.

Illustratively, the prescription dose will vary according to the type and location of the cancer cells. The value of the dose is generally determined based on the particular characteristics of the tumor. In general, the value of the prescription dose may be input by an attending physician. Of course, the value of the prescription dose may also be selected based on the parameter values of the tumor by referring a previously stored template.

A second determination module 204 is configured for determining a therapeutic head, a therapeutic approach and a therapeutic drive approach suitable for irradiating the target region, based on the therapeutic target region and the prescription dose thereof. Wherein, the therapeutic approach comprises at least the type of irradiation technique, time of irradiation and shape of an irradiation field, the therapeutic drive approach comprises synchronous drive approach and asynchronous drive approach, wherein the synchronous drive approach represents emitting radiation beam simultaneously or alternately and completing a treatment by both of the at least two therapeutic heads at the same time period; the asynchronous drive approach represents completing the treatment in different steps each with a therapeutic head, and a treatment process is started after a completion of another treatment process.

Wherein, the therapeutic approach comprises the type of irradiation technique, time of irradiation and shape of an irradiation field. Illustratively, the therapeutic drive approach comprises a synchronous drive approach and an asynchronous drive approach. Wherein, the synchronous drive approach represents emitting radiation beam simultaneously or alternately and completing a treatment by both of the two therapeutic heads at the same time period. For example, using the conformal therapeutic head to perform a conformal treatment to a large area of the tumor, and using the focused therapeutic head to perform a dose enhancement treatment on part of the tumor, increasing the local dose of the tumor, e.g. applying the local dose enhancement treatment to the anoxic region, the tumor cell intensive region, or the like. The asynchronous drive approach represents completing the treatment in different steps each with a therapeutic head, and, a treatment process is started after a completion of another treatment process. For example, if the tumor is large, the conformal therapeutic head is applied at first for large-scale conformal treatment. In the irradiation process, if part of the tumor region receives less dose due to uneven dose distribution, or it is needed to perform dose-enhanced to the anoxic region and/or tumor cell intensive areas, the local dose-enhanced radiation therapy can be started with the focused therapeutic head after completing the conformal treatment.

The irradiation technology refers to different irradiation methods, including whole-arc irradiation, partial-arc irradiation and directional irradiation with the focused therapeutic head, etc., and also including a three-dimensional conformal treatment, stereotactic intensity modulated therapy and intensity modulated arc therapy of the conformal therapeutic head, and so on.

Figure 14:
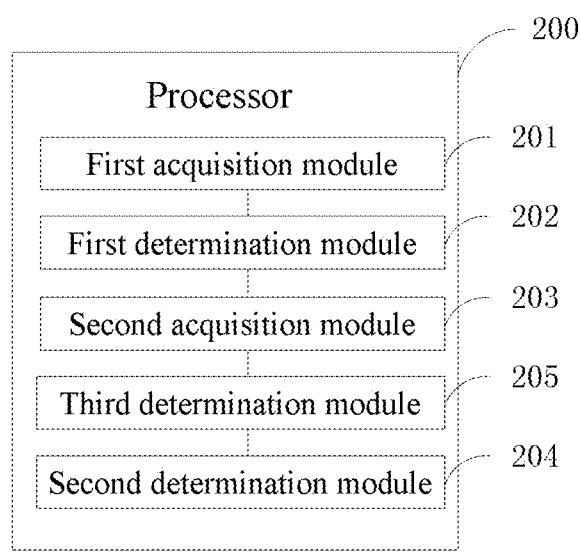
FIG. 14 is a schematic diagram of the processor in accordance with another embodiment of the present disclosure.

Refer to FIG. 14, the processor further includes: a third determination module 205, configured for dividing the treatment target region to identify at least one sub-region.

Take FIG. 5 as an example, the treatment target region 310 is subdivided, e.g., the treatment target region 310 is divided with a sub-region 311 as an anoxia region and other regions excluding the sub-region 311. In order to achieve the effect of eliminating the tumor, the local dose of the sub-region 311 should be more than the dose for other regions. In the radiation treatment plan generation method of the present disclosure, a conformal treatment of the tumor could be performed by the conformal therapeutic head, and at the same time, the local dose enhancement treatment for each sub-region could be performed by the focused therapeutic head. For example, the multi-leaf collimator may be conformed to form a beam-passable region similar to the tumor 31, and the radiation source of the conformal therapeutic head emits a radiation beam that is illuminated on the body through the beam-passable region, to form a treatment target region 310 shown in FIG. 5. As such, the treatment target region 310 can be treated with a conformal therapy. The focal point of focused therapeutic head is then directed toward the sub-region, thereby enhancing the dose of the sub-region.

The second determination module 204 in this embodiment applies the conformal treatment to the treatment target region by the conformal therapeutic head and applies the dose enhancement treatment to the sub-region by using the focused therapeutic head.

The prescription dose further comprises a parameter of prescription dose distribution that represents a dose that should be received in different sub-regions of the therapeutic target.

In the case where the therapeutic target region comprises two or more sub-regions, the second determination module 204 is further configured for performing the dose enhancement treatment for at least two of the sub-regions. And the therapeutic approach of the focused therapeutic head further comprises moving the focal point to different sub-regions.

Illustratively, if the synchronous drive approach is employed with the focused therapeutic head and the conformal therapeutic head to perform a radiation therapy to the tumor as shown in FIG. 6, the conformal therapeutic head may be employed to conformally irradiate the target region, and during the conformal irradiation process, the focused therapeutic head may be moved between the sub-region 311 and the sub-region 312, such that both the sub-region 311 and the sub-region 312 undergo local dose enhancement.

In the case where the therapeutic target region comprises a plurality of disconnected sub-regions, the second determination module 204 is further configured for applying different therapeutic heads to different sub-regions.

As shown in FIG. 7, the sub-region 313 may be subjected to conformal treatment using a conformal therapeutic head, and the sub-region 314 may be applied the focused irradiation treatment using the focused therapeutic head. In general, in a case where the widest diameter of the target region is equal to or more than 5 cm, the treatment is performed using the conformal therapeutic head; and when the widest diameter of target region is less than 5 cm, the treatment is performed using the focused therapeutic head.

Figure 15:
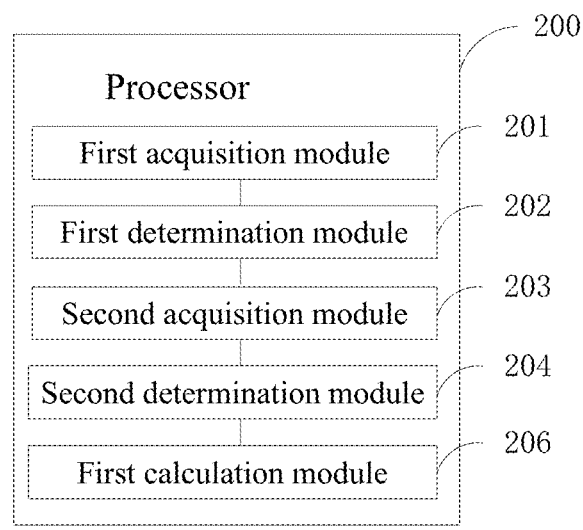
FIG. 15 is a schematic diagram of the processor in accordance with another embodiment of the present disclosure.

As shown in FIG. 15, the processor includes a first calculation module 206, configured for calculating a predicted dose for the target region, and determining whether the predicted dose for the therapeutic target region meets a requirement for the prescription dose. If the predicted dose does not meet the requirement for the prescription dose, at least one of the therapeutic head, the therapeutic approach, and the therapeutic drive approach is adjusted.

Wherein, the predicted dose received by the tumor is generally measured according to the radiation dose of the beams emitted from the radiation source and the dose of the beam through the body, to determine whether the dose meets the prescription dose requirements. In general, the predicted dose corresponds to the prescription dose. For example, if the prescription dose includes a parameter of prescription dose value and a parameter of prescription dose distribution, the predicted dose may include a parameter of predicted dose value and a parameter of predicted dose distribution. In the present disclosure, the dose distribution of a patient after treatment is predicted based on the dose calculation approach, to determine whether dose distribution meets the prescription dose requirements, to further determine whether the treatment of patients can achieve the desired therapeutic effect.

Figure 16:
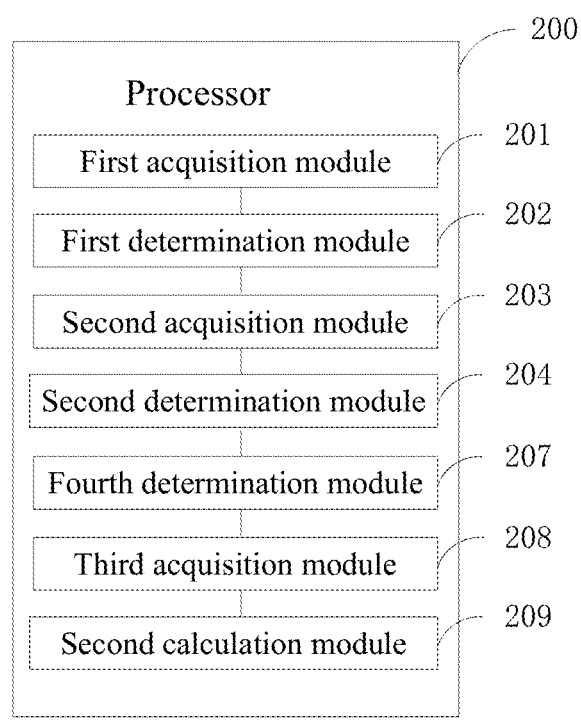
FIG. 16 a schematic diagram of the processor in accordance with another embodiment of the present disclosure.

As shown in FIG. 16, the processor further includes a fourth determination module 207, a third acquisition module 208, and a second calculation module 209.

The fourth determination module 207 is configured for determining at least part of the vital organs surrounding the treatment target region based on the acquired images.

The third acquisition module 208 is configured for obtaining the corresponding dose limits for the vital organs.

The second calculation module 209 is configured for calculating a predicted dose for each of the vital organs based on the determined therapeutic head, therapeutic approach, and therapeutic drive approach, to determine whether the predicted dose for the vital organ exceeds the dose limit therefor. If the predicted dose exceeds the dose limit of the vital organ, at least one of the therapeutic head, the therapeutic approach, and the therapeutic drive approach is adjusted.

The radiotherapy equipment includes two conformal therapeutic heads. The third determination module 205 is further configured for dividing the treatment target region to identify at least one sub-region. The second determination module 204 is further configured for applying a conformal treatment to the treatment target region by one of the conformal therapeutic heads, and applying a dose enhancement treatment to the at least one sub-region by using another conformal therapeutic head.

Furthermore, the processor is further configured for receiving the actual dose of the radiation beams during the dose verification, and comparing the actual dose of the radiation beam with the prescription dose. When the verification result does not meet the requirement of the prescription dose, at least one of the therapeutic head, the therapeutic approach, and the therapeutic drive approach is adjusted.

Illustratively, the actual dose of the radiation beams can be transmitted to the processor by the detector, and the processor would compare the actual dose of the radiation beams with the prescription dose, to determine whether the actual dose meets the requirements of the prescription dose. If not, the processor or the attending physician could adjust and optimize the treatment plan.

The steps of the method or algorithm described in the present disclosure may be implemented in hardware, or in a manner that the processor executes software instructions. The software instructions may be composed of corresponding software modules which may be stored in a random access memory (RAM), a flash memory, a read only memory (ROM), an erasable programmable read only memory (EPROM), electrically programmable read only memory (EEPROM), registers, hard disk, removable hard disk, CD-ROM, or any other form of storage medium known in the art. An exemplary storage medium is coupled to the processor such that the processor can read information from and write information to the storage medium. Of course, the storage medium can also be an integral part of the processor. The processor and the storage medium may be located in ASIC. In addition, the ASIC may be located in a core network interface device. Of course, the processor and the storage medium may also exist as discrete components in the core network interface device.

It should be appreciated by those skilled in the art that the functions described herein may be implemented in hardware, software, firmware, or any combination thereof, in one or more of the above-described examples. When implemented using software, these functions may be stored on a computer-readable medium or transmitted as one or more instructions or code on a computer-readable medium. The computer-readable medium includes a computer storage medium and a communication medium, wherein the communication medium includes any medium that facilitates transfer of a computer program from one place to another. The storage medium may be any available medium that can be accessed by a general purpose or special purpose computer.

Take the method of FIG. 3 as an example, the present disclosure provides a nonvolatile computer-readable storage medium. When the instructions in the storage medium are executed in the processor of the treatment planning system, the treatment planning system enables the radiation treatment plan generation method. Particularly, the method comprises the steps of S101 to S104.

In step S101, body images of the patient are acquired. The body image includes an image of the tumor.

In step S102, the treatment target region is determined based on the acquired body image. The treatment target region comprises the tumor and is a region being irradiated with the radiation beams during radiotherapy.

In step S103, the prescription dose of the treatment target region is obtained.

Wherein the prescription dose comprises a parameter of prescription dose value, which is the magnitude of the dose that the tumor should be received in order to achieve a therapeutic effect.

In step S104, a therapeutic head, a therapeutic approach and a therapeutic drive approach suitable for irradiating the target region are determined based on the treatment target region and the prescription dose thereof.

Wherein, the therapeutic approach comprises the type of irradiation technique, time of irradiation and shape of an irradiation field. Illustratively, the therapeutic drive approach comprises a synchronous drive approach and an asynchronous drive approach. Wherein, the synchronous drive approach represents emitting radiation beam simultaneously or alternately and completing a treatment by both of the two therapeutic heads at the same time period. The asynchronous drive approach represents completing the treatment in different steps each with a therapeutic head, and a treatment process is started after a completion of another treatment process.

Of course, when the instructions in the nonvolatile computer-readable storage medium are executed in the processor of the treatment planning system, the treatment planning system may enable another radiation treatment plan generation method. The method may be any one of the methods shown in FIG. 4, and FIGS. 8-12.

A specific structure of the radiotherapy equipment of the present disclosure, which is applied to the radiation treatment plan generation method and the treatment planning system, will be exemplified as below. Of course, the structure or configuration of the radiotherapy apparatus is not limited to this. For example, the focused therapeutic head and the conformal therapeutic head may be structured with an included angle for 90 degree.

Illustratively, the embodiments described above may be applied to the radiotherapy equipment shown in FIG. 1 and FIG. 2. The radiotherapy equipment 100 comprises a base 50, a gantry 40, a focused therapeutic head 10, a conformal therapeutic head 20, and a treatment couch 60. The base 50 supports the whole radiotherapy equipment 100, and plays a role of carrying the whole radiotherapy equipment 100 and a role of fixation. The treatment couch 60 is arranged on the base 50, and is movably connected to the base 50, e.g. by screws and/or pins. The treatment couch 60 is used to support and position a patient, and can accurately deliver the patient to a specified position for treatment. The gantry 40 is arranged on the base 50, and is connected to the base 50 by a rolling support. The gantry 40 rotates around an axial line by means of, e.g. gear driving.

As shown in FIGS. 1 and 2, the focused therapeutic head 10 and the conformal therapeutic head 20 are distributed at both sides of the axis of the gantry 40. Because the gantry 40 rotates around the axis line (i.e. the gyration center) thereof, the focused therapeutic head 10 and the conformal therapeutic head 20 are driven to continuously or reciprocally rotate 360 degrees around the axis line (i.e. the gyration center) of the gantry 40. In addition, the two types of therapeutic heads are connected to the gantry 40 and movable along an axial direction of the gantry 40, via respective arc guide rail 70. In this way, the therapeutic heads 10 and 20 may continuously translated around the focal point on a gantry axial plane, and a translation angle is in a range of 0 to ±47.5 degrees, so as to implement non-coplanar focusing or conformal therapy with different incident angles, thereby carrying out tumor therapy more flexibly and effectively. Further, regarding the placement of the focused therapeutic head 10 and the conformal therapeutic head 20, an included angle therebetween is continuously adjustable between 30 degrees and 180 degrees. Illustratively, the included angle is 90 degrees. Since the therapeutic heads can make a continuous incident angle change of maximum ±47.5 degrees and a central rotation of 360-degree around the axis, a treatment incident angle of the system may exceed $2\pi$.

The focused therapeutic head 10 further includes a plurality of radioactive sources, a movable collimator, and a pre-collimator. In the embodiment of the present disclosure, the radioactive sources adopt cobalt-60, to generate gamma rays. The gamma rays generated by the cobalt-60 pass through the pre-collimator and the movable collimator, and are focused on the focal point. As such, a focused field, namely, a high-dose region for therapy, is formed. The movable collimator is provided with a plurality of apertures in different size. The movement of the movable collimator is performed to switch the apertures, so as to change a size and a shape of the focused field. As such, the focused therapeutic head 10 can be used to implement accurate therapy with a small field size and a high dose.

The conformal therapeutic head 20 comprises a radioactive source, a pre-collimator, and a multi-leaf collimator. In the embodiment of the present disclosure, the radioactive source may be a single cobalt source or an X ray generator having an intensity greater than 4 mV. The radioactive source cooperates with the multi-leaf collimator to implement different field shapes on a treatment plane, so as to implement three-dimensional adaptive intensity modulated irradiation. The multi-leaf collimator is implemented with generally used technology, and details will not be described in the embodiment of the present disclosure.

The focused therapeutic head may perform Stereotaxic Radiosurgery (SRS) or Imaging Guide Radiation Therapy (IGRT). The conformal therapeutic head may perform 3-Dimensional Conformal Radiation Therapy (3D-CRT), or Intensity Modulated Radiation Therapy (IMRT), or Stereotactic Body Radiation Therapy (SBRT), or Imaging Guide Radiation Therapy (IGRT).

In addition, the radiotherapy equipment 100 of the present disclosure further comprises a dynamic image guide system (IGS). In this embodiment, one or two sets of stereo imaging apparatuses (i.e. X-ray generator and image detection and acquisition system) are assembled on the rotatable gantry 40 through focusing to the same focal point. Accordingly, the one or two sets of X-ray imaging apparatuses are configured to perform real-time detection of a body position and a focus space position of a patient. Space position compensation is performed for the treatment couch and the therapeutic heads according to a detection result, so as to ensure high-precision orientation during treatment and implement accurate radiation therapy. When two sets of X-ray imaging apparatuses are adopted, an included angle of two sets of imaging apparatuses is in a range of 20 degrees to 160 degrees.

In the embodiment of the present disclosure, the focused therapeutic head with multi-source and the conformal therapeutic head with intensity modulation are integrated into one therapeutic equipment, having a great advantage for some special tumor focuses where two manners of focused treatment and conformal treatment are simultaneously or separately required. In the therapeutic equipment, the conformal therapeutic head and the focused therapeutic head with multi-source may be simultaneously or separately used for irradiation therapy with one time positioning, to implement two types of radiation therapy in combination, errors caused by multiple times of positioning are reduced, and radiation therapy precision and speed are improved, thereby improving quality and efficiency.

The present invention has been described in further detail with reference to the specific embodiments described above, and it is to be understood that the foregoing is intended only as a specific embodiment of the invention and is not intended to limit the scope of the invention. The scope of protection of the present invention is to be understood to be within the scope of the present invention as defined by the equivalents thereof or equivalents thereof or to any other related art, either directly or indirectly, by the use of the present specification and drawings.

What is claimed is:

1. A method for generating a radiation treatment plan, applied to a therapeutic equipment comprising at least two therapeutic heads, the method comprising the steps of:
    acquiring images of an area of a patient with a tumor;
    determining a therapeutic target region including the tumor as a region for being irradiated with radiation beams upon radiotherapy, based on the acquired images;
    obtaining a prescription dose corresponding to the therapeutic target region, wherein the prescription dose comprises a parameter of prescription dose value that is a magnitude of a dose received by the tumor;
    determining at least one of the therapeutic heads a therapeutic approach and a therapeutic drive approach suitable for irradiating the target region, based on the therapeutic target region and the prescription dose thereof, to preliminarily generate the radiation treatment plan; wherein, the therapeutic approach comprises at least a type of irradiation technique, time of irradiation and shape of an irradiation field, the therapeutic drive approach comprises synchronous drive approach and asynchronous drive approach, wherein the synchronous drive approach represents emitting radiation beams simultaneously or alternately and completing a treatment by both of the at least two therapeutic heads at the same time period; the asynchronous drive approach represents completing the treatment in different steps each with a therapeutic head, and a treatment process is started after a completion of another treatment process; and
    performing a dose verification for the preliminarily generated radiation treatment plan.

2. The method of claim 1, wherein the at least two therapeutic heads comprises at least one focused therapeutic head and at least one conformal therapeutic head.

3. The method of claim 2, wherein, prior to the determination of the therapeutic head, the therapeutic approach and the therapeutic drive approach suitable for the target region and after the step of determining the therapeutic target region, the method further comprises steps of:
    dividing the therapeutic target region to identify at least one sub-region;
    wherein the prescription dose further comprises a parameter of prescription dose distribution that represents a dose that should be received in different sub-regions of the therapeutic target: and
    the step of determining the therapeutic head, the therapeutic approach and the, therapeutic drive approach suitable for the target region comprises:
    applying a conformal treatment to the therapeutic target region by the conformal therapeutic head and applying a dose enhancement treatment to the at least one sub-region by using the focused therapeutic head.

4. The method of claim 3, wherein in the case where the therapeutic target region comprises two or more sub-regions, the step of applying dose enhancement treatment to the sub-region by using the focused therapeutic head comprises:
    performing the dose enhancement treatment for at least two of the sub-regions;
    wherein the therapeutic approach of the focused therapeutic head further comprises moving a focal point to different sub-regions.

5. The method of claim 3, wherein in the case where the therapeutic target region comprises a plurality of disconnected sub-regions, the step of determining the therapeutic head suitable for the target region comprises:
    applying different therapeutic heads to different sub-regions.

6. The method of claim 5, wherein in a case where the widest diameter of the target region is equal to or more than 5 cm, the treatment is performed using the conformal therapeutic head; and when the, widest diameter of target region is less than 5 cm, the treatment is performed using the focused therapeutic head.

7. The method of claim 1, further comprising:
    calculating a predicted dose for the target region based on the determined therapeutic head, therapeutic approach, and therapeutic drive approach, to determine whether the predicted dose for the therapeutic target region meets a requirement for the prescription dose; and
    adjusting at least one of the therapeutic head, the therapeutic approach, and the therapeutic drive approach while the predicted dose does not meet the requirement for the prescription dose.

8. The method of claim 1, further comprising:
    determining at least, part of vital organs surrounding the therapeutic target region based on the acquired images;
    obtaining corresponding dose limits for the vital organs;
    calculating a predicted dose for each of the vital organs based on a determined therapeutic head, therapeutic approach, and therapeutic drive approach, to determine whether the predicted dose for the vital organ exceeds the dose limit therefor, and
    adjusting at least one of the therapeutic head, the therapeutic approach, and the therapeutic drive approach while the predicted dose exceeds the dose limit of the vital organ.

9. The method of claim 1, wherein the dose verification comprises:
    receiving the, radiation beams from the corresponding therapeutic head by a detector, and measuring an actual dose of the radiation beams, wherein the actual dose including a parameter of dose value;
    comparing the actual dose of the radiation beams to the prescription dose; and
    adjusting at least one of the therapeutic head, the therapeutic approach, and the therapeutic drive approach if the verification result does not meet a requirement of the prescription dose.

10. The method of claim 1, wherein the radiotherapy equipment comprises two conformal therapeutic heads, and after the step of determining a therapeutic target region, the method further comprises:
dividing the therapeutic target region to identify at least one sub-region;
the step of determining the therapeutic head and the therapeutic approach suitable for the target region comprises:
applying a conformal treatment to the therapeutic target region by one of the conformal therapeutic heads, and applying a dose enhancement treatment to the at least one sub-region by using another conformal therapeutic head.

11. A radiation treatment planning system, applied to a therapeutic equipment comprising at least two therapeutic heads, comprising a processor configured for:
acquiring images of an area of a patient with a tumor;
determining a therapeutic target region including the tumor as a region for being irradiated with radiation beams upon radiotherapy, based on the acquired images;
obtaining a prescription dose corresponding to the therapeutic target region, wherein the prescription dose comprises a parameter of prescription dose value that is a magnitude of a dose received by the tumor;
determining at least one of the therapeutic heads, a therapeutic approach and a therapeutic drive approach suitable for irradiating the target region, based on the therapeutic target region and the prescription dose thereof, to preliminarily generate a radiation treatment plan; wherein the therapeutic approach comprises at least a type of irradiation technique, time of irradiation and shape of an irradiation field, the therapeutic drive approach comprises synchronous drive approach and asynchronous drive approach, wherein the synchronous drive approach represents emitting radiation beam simultaneously or alternately and completing a treatment by both of the at least two therapeutic heads at the same time period; the asynchronous drive approach represents completing the treatment in different steps each with a therapeutic head, and a treatment process is started after a completion of another treatment process; and
performing a dose verification for the preliminarily generated radiation treatment plan.

12. The radiation treatment planning system of claim 11, wherein the at least two therapeutic heads comprises at least one focused therapeutic head and at least one conformal therapeutic head.

13. The radiation treatment planning system of claim 12, wherein, the processor is further configured for:
dividing the therapeutic target region to identify at least one sub-region; and
applying a conformal treatment to the therapeutic target region by the conformal therapeutic head and applying a dose enhancement treatment to the at least one sub-region by using the focused therapeutic head;
wherein the prescription dose further comprises a parameter of prescription dose distribution that represents a dose that should be received in different sub-regions of the therapeutic target.

14. The radiation treatment planning system of claim 13, wherein in the case where the therapeutic target region comprises two or more sub-regions, the processor is further configured for performing the dose enhancement treatment for at least two of the sub-regions;
wherein the therapeutic approach of the focused therapeutic head further comprises moving a focal point to different sub-regions.

15. The radiation treatment planning system of claim 13, wherein in the case where the therapeutic target region comprises a plurality of disconnected sub-regions, the processor is further configured for applying different therapeutic heads to different sub-regions.

16. The radiation treatment planning system of claim 11, wherein the processor is further configured for:
calculating a predicted dose for the target region based on the determined therapeutic head, therapeutic approach, and therapeutic drive approach, to determine whether the predicted dose for the therapeutic target region meets a requirement for the prescription dose; and
adjusting at least one of the therapeutic head, the therapeutic approach, and the therapeutic drive approach while the predicted dose does not meet the requirement for the prescription dose.

17. The radiation treatment planning system of claim 11, wherein the processor further configured for:
determining at least part of vital organs surrounding the therapeutic target region based on the acquired images;
obtaining corresponding dose limits for the vital organs;
calculating a predicted dose for each of the vital organs based on a determined therapeutic head, therapeutic approach, and therapeutic drive approach, to determine whether the predicted dose for the vital organ exceeds the dose limit therefor; and
adjusting at least one of the therapeutic head, the therapeutic approach, and the therapeutic drive approach while the predicted dose exceeds the dose limit of the vital organ.

18. The radiation treatment planning system of claim 11, wherein the radiotherapy equipment comprises two conformal therapeutic heads, and the processor is further configured for dividing the therapeutic target region to identify at least one sub-region, and applying a conformal treatment to the therapeutic target region by one of the conformal therapeutic heads, and applying a dose enhancement treatment to the at least one sub-region by using another conformal therapeutic head.

19. The radiation treatment planning system of claim 11, wherein the processor is configured for:
receiving an actual dose of the radiation beams during the dose verification, and comparing the actual dose of the radiation beam to the prescription dose; and
adjusting at least one of the therapeutic head, the therapeutic approach, and the therapeutic drive approach if the verification result does not meet a requirement of the prescription dose.

* * * * *

UNITED STATES PATENT AND TRADEMARK OFFICE
CERTIFICATE OF CORRECTION

PATENT NO. : 10,806,949 B2
APPLICATION NO. : 15/351494
DATED : October 20, 2020
INVENTOR(S) : Jinsheng Li et al.

Page 1 of 1

It is certified that error appears in the above-identified patent and that said Letters Patent is hereby corrected as shown below:

On the Title Page

After item "(65) Prior Publication Data US 2018/0133516 A1 May 17, 2018", insert the following:
--Related U.S. Application Data
(63) Continuation-in-part of application No. 14/437,333 filed on April 21, 2015, now Pat. No. 9,526,919--.

Signed and Sealed this
Twenty-ninth Day of December, 2020

Andrei Iancu
*Director of the United States Patent and Trademark Office*